United States Patent [19]

Cunningham et al.

[11] Patent Number: 5,581,010
[45] Date of Patent: Dec. 3, 1996

[54] SEMI-ORGANIC CRYSTALS FOR NONLINEAR OPTICAL DEVICES

[75] Inventors: Patricia H. Cunningham, Thousand Oaks; Leslie F. Warren, Jr.; Henry O. Marcy, 5th, both of Camarillo; Mark J. Rosker, Newbury Park, all of Calif.

[73] Assignee: Rockwell International Corporation, Seal Beach, Calif.

[21] Appl. No.: 278,741

[22] Filed: Jul. 22, 1994

[51] Int. Cl.$^6$ .................... C07F 5/04; G02F 1/03
[52] U.S. Cl. .................... 558/290; 359/256
[58] Field of Search .................... 558/290

[56] References Cited

U.S. PATENT DOCUMENTS

| | | | |
|---|---|---|---|
| 2,480,814 | 8/1949 | Punshon et al. | 260/794 |
| 2,582,191 | 1/1952 | Curtis | 558/290 X |
| 2,902,450 | 9/1959 | Lowe | 558/290 X |
| 3,373,170 | 3/1968 | Jones | 558/290 X |
| 3,403,104 | 9/1968 | Sullivan | 558/290 X |
| 3,539,614 | 11/1970 | Ross et al. | 558/290 |
| 3,772,357 | 11/1973 | Hamanaka | 558/290 X |
| 3,860,626 | 1/1975 | Putnin et al. | 558/290 |
| 3,949,323 | 4/1976 | Bierlein et al. | 332/7.51 |
| 4,376,899 | 3/1983 | Chemla et al. | 307/425 |
| 4,818,898 | 4/1989 | Anderson et al. | 307/427 |
| 4,839,536 | 6/1989 | Etter et al. | 307/425 |
| 4,931,457 | 6/1990 | Effland et al. | 514/349 |
| 5,123,022 | 6/1992 | Ebbers et al. | 372/22 |

FOREIGN PATENT DOCUMENTS

| | | | |
|---|---|---|---|
| 662773 | 5/1963 | Canada | 260/429 |
| 0389879 | 10/1990 | European Pat. Off. | G02F 1/35 |

OTHER PUBLICATIONS

Anderson, et al., Chemical Physics Letters, vol. 134, p. 392 (1987).
Andreetti, et al., Acta Crysta, vol. B24, p. 683 (1968).
Guangcai, et al., Chinese Physics–Lasers, vol. 14, p. 357 (1987).
Marcotrigiano, et al., Journal of Inorganic Nuclear Chemistry, vol. 36, p. 3719 (1974).

(List continued on next page.)

Primary Examiner—Johann Richter
Assistant Examiner—Michael G. Ambrose
Attorney, Agent, or Firm—John J. Deiken; George A. Montanye; Jim P. O'Shaughnessy

[57] ABSTRACT

A nonlinear optical material includes a noncentrosymmetric crystal of an anionic boron complex salt containing a cation and at least one organic ligand coordinated to a boron atom. The nonlinear optical crystal may consist of a compound having the formula $A[BC_2]$ where A is a monocation, B is boron, and C is the organic ligand, or a compound having the formula $A[BC_2]_2$ where A is a dication, B is boron, and C is the organic ligand. The organic ligands may also be organic molecules having α-dihydroxy functionalities. Furthermore, the organic ligands may be selected from the group consisting of α-hydroxy carboxylic acids and 1,2-diols or from the group consisting of d-malic acid, d-lactic acid, d-tartaric acid, dimethyl-d-tartrate, diethyl-d-tartrate, l-malic acid, l-lactic acid, l-tartaric acid, dimethyl-l-tartrate, diethyl-l-tartrate, and ethylene glycol. The anionic boron complex may be selected from the group consisting of boro-di(l-malate), boro-di(l-tartrate), boro-di(l-lactate), boro-di(diethyl-l-tartrate), boro-di(methyl-1-tartrate), boro-di(d-tartrate), boro-di(d-lactate), boro-di(diethyl-d-tartrate), boro-di(dimethyl-d-tartrate) and boro-di(ethylene glycolate). The cation may be selected from the group consisting of alkali metals, alkaline earth metals, ammonium ions, and Group 2B dications. The cation may be further selected from the group consisting of lithium, sodium, potassium, the ammonium $NH_4^+$ ion, the guanidinium $C(NH_2)_3^+$ ion, calcium, and zinc.

1 Claim, 3 Drawing Sheets

OTHER PUBLICATIONS

Marcy, Applied Optics, vol. 31, p. 5051 (1992).
Marcy, et al., Materials Research Society Symposium Proceedings, vol. 228, p. 351 (1992).
Newman, et al., Materials Research Soceity Symposium Proceedings, vol. 173, p. 557 (1990).
Perret, et al., Materials Research Bulletin, vol. 21, p. 1397 (1986).
Sigelle, et al., Journal of Non–Crystalline Solids, vol. 47, P. 287 (1982).
Wang, et al., Japanese Journal of Applied Physics, vol. 27 p. 1138 (1988).
Warren, in Electronic Materials–Our Future, Proceedings of 4th International SAMPE Electronics Conference, vol. 4, p. 388 (Allred, et al. eds., 1990).

SEMI-ORGANIC CRYSTALS FOR NONLINEAR OPTICAL DEVICES

BACKGROUND OF THE INVENTION

This invention relates to the field of optics and particularly to materials for use as a nonlinear element in nonlinear optical devices.

Recent advances in nonlinear optics (NLO) have created a new frontier for applied optics. This technology requires nonlinear optical materials, i.e., materials which alter the frequency of laser light, materials which have an index of refraction that varies with light intensity or with applied electrical field, or (in the case of photorefractive nonlinear optical materials) materials which have a local index of refraction that is changed by the spatial variation of light intensity.

Devices which have been conceived utilizing NLO materials include parametric amplifiers, oscillators, second harmonic generators, and modulators. Such devices provide, inter alia, second harmonic generation, phase-conjugate navigation, and laser beam combining which employs optical phase conjugation, as well as laser beam spatial (and spectral) mode cleanup, wavelength agile rejection filtering, laser radar, image correlation and enhancement, communications, optical data storage, and optical computing. In particular, there are readily identifiable systems applications which need lower-cost, higher-response, higher-average-power materials for optical parametric amplifier operation and second harmonic generation throughout the blue/near-ultraviolet spectral region. Bierlein, et al., U.S. Pat. No. 3,949,323, for example, depicts, in FIG. 1, the use of a nonlinear optical material to generate second harmonic radiation and, in FIG. 2, the use of such a material to modulate the intensity of a beam of polarized light. Many of these concepts rely on real-time holographic effects which can be induced in nonlinear materials. Although several of these innovations are at preliminary stages of design, such concepts reveal the power of nonlinear optics in terms of performance breakthroughs in electro-optic device technology that a decade ago would have been thought impossible.

The manufacturability of nonlinear optical devices, however, is limited by the performance of currently available NLO materials, which are primarily inorganic oxide crystals such as potassium niobate, potassium dihydrogen phosphate, lithium niobate, strontium barium niobate, and barium titanate. These inorganic oxide crystals exhibit shortcomings as nonlinear materials due to difficulty of synthesis, lack of optical quality, and slow electro-optic response times.

Although there are many organic materials (for example, urea and 2-methyl-4-nitroaniline) which exhibit very high second harmonic generation responses in powder form, there have been no practical device-quality organic NLO crystals available in the art. Typical organic crystals lack the mechanical robustness, dimensional and thermal properties, and optical quality required for fabricating optical devices.

A category of "semi-organic materials", or metal-organic coordination complexes, has been reported to show promise in the development of nonlinear optical materials. See, for example, Wenbo et al., A new organometallic nonlinear optical material-triallylthiourea mercury bromide (ATMB) crystal: growth and structure, Journal of Crystal Growth, Volume 133, Page 71 (1993) and Dong, et al., A New Aromatic Organometallic Nonlinear Optical Crystal: [Bis-4-nitropyridine-N-oxide Cadmium Chloride], Materials Research Bulletin, Volume 29, Page 73 (1994). This materials classification encompasses a very large number of semi-organic ionic crystals in which relatively large, polarizable organic molecules are incorporated into a host inorganic ionic lattice.

Advanced nonlinear optical (NLO) applications such as high speed optical phase conjugation, parametric amplification, and laser hardening require NLO crystals having high speed and high efficiency. Devices for these applications require new and improved NLO crystals in order to achieve their potential.

SUMMARY OF THE INVENTION

A nonlinear optical material includes a noncentrosymmetric crystal of an anionic boron complex salt containing a cation and at least one organic ligand coordinated to a boron atom.

In more particular embodiments, the nonlinear optical crystal consists of a compound having the formula $A[BC_2]$, where A is a monocation, B is boron, and C is the organic ligand, or a compound having the formula $A[BC_2]_2$ where A is a dication, B is boron, and C is the organic ligand.

In another embodiment, the organic ligands are organic molecules having α-dihydroxy functionalities. Furthermore, the organic ligands may be selected from the group consisting of α-hydroxy carboxylic acids and 1,2-diols or from the group consisting of d-malic acid, d-lactic acid, d-tartaric acid, d-dimethyl tartrate, d-diethyl tartrate, l-malic acid, l-lactic acid, l-tartaric acid, l-dimethyl tartrate, l-diethyl tartrate, and ethylene glycol. The anionic boron complex may be selected from the group consisting of boro-di(l-malate), boro-di(l-tartrate), boro-di(l-lactate), boro-di(diethyl-l-tartrate), boro-di(d-malate), boro-di(d-tartrate), boro-di(d-lactate), boro-di(diethyl-d-tartrate), and boro-di(ethylene glycolate).

In another alternative embodiment, the cation is selected from the group consisting of alkali metals, alkaline earth metals, ammonium ions, and Group 2B dications. The cation may be further selected from the group consisting of lithium, sodium, potassium, the ammonium $NH_4^+$ ion, the guanidinium $C(NH_2)_3^+$ ion, calcium, and zinc.

DESCRIPTION OF THE INVENTION

Figure 1:
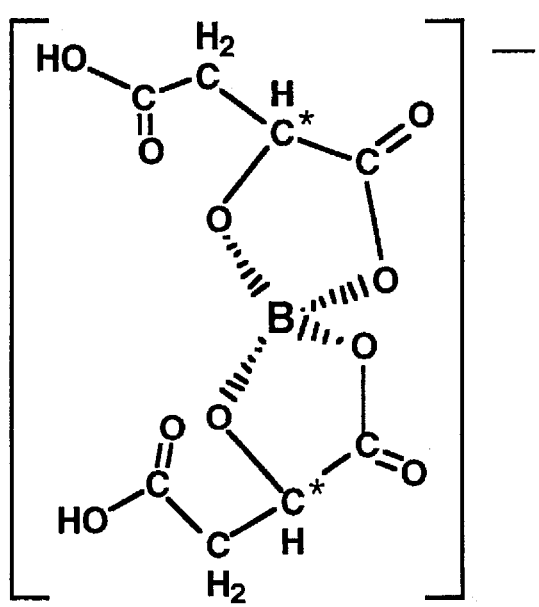
FIG. 1 is a representation of the boromalate anion.

Organic materials provide an opportunity for making relatively low-power laser-driven nonlinear optical (NLO) systems feasible because of the potentially large magnitudes of their optical nonlinearities and other favorable optical properties, such as optical response time, non-resonant susceptibility, second harmonic generation, and high phase-conjugate reflectivity. With the diversity of molecular structure and composition available through organic synthesis, there is an extremely high flexibility in material design with organic materials, allowing both NLO effects and processing properties to in principle be optimized through molecular engineering. Although detailed studies of prototype organics have been reported, specific overall molecular design criteria useful to chemists have not yet been developed. A primary impediment to implementing a molecular design approach is the inability to predict the molecular orientation or crystal structure of a new compound. Such features are crucial to observing high nonlinear efficiencies. In addition, it is not currently possible to predict the refractive index dispersion or the birefringence, or to assess the mechanical and chemical properties of materials from knowledge of the molecular structure.

Required physical and chemical properties other than NLO properties can severely limit the utility of pure organic materials. For certain nonlinear optical applications, for example, large optical quality crystals are desired (large clear crystals at least 4 mm on a side are typically required, with appropriate morphology, i.e., long thin needles are unacceptable). The crystals must form easily and be physically robust to facilitate good cutting and polishing and thereby reduce light diffusion and increase the threshold of surface damage. These properties will ultimately determine whether a NLO material is suitable for the fabrication of practical devices. Unfortunately, most pure organic compounds lack physical robustness, have low dimensional properties, and exhibit poor three-dimensional bonding which leads to low crystal quality.

It is an outstanding feature of this invention to combine the nonlinear optical advantages of organic materials with the advantages of inorganic materials by utilizing semi-organic salt crystals. These semi-organic salts reside in a general class of materials called coordination complexes, some of which can be polymeric in the solid state (via bridging ligand atoms and hydrogen bonding). In these crystals, organic molecules are incorporated into an inorganic salt lattice and/or in a coordination complex salt. Typically, an inorganic counterion (for example, phosphate, sulfate, etc.) is used to provide the inorganic host lattice. Compared to conventional neutral organics, very large ionic single crystals can be relatively easily grown with the appropriate selection of a counterion. Such a marriage of organics and inorganics in ionic salts, in addition to providing the fast optical response times of some organic type materials, was predicted to also exhibit low frequency NLO responses by virtue of lattice distortions.

The boromalate salts, with the exception of potassium boromalate hydrate (KBM), which is known to be monoclinic $P2_1$, are crystals whose structures and optical properties have not previously been examined. All are examples of "semiorganic" NLO materials in which the high optical nonlinearity of a purely organic material is combined with the favorable mechanical and thermal properties of an inorganic (Marcy, et al., Applied Optics, Volume 31, Pages 5051–5060 (1992); Warren, in Electronic Materials-Our Future, Proceedings of the 4th International SAMPE Electronics Conference, Volume 4, Pages 388–396 (Allred, et al. eds., 1990)). Much recent work (e.g., Meredith, in Nonlinear Optical Properties of Organic and Polymeric Materials, American Chemical Society Symposium Series, Volume 233, Pages 27–156 (Williams ed., 1982); Materials for Nonlinear Optics-Chemical Perspectives, American Chemical Society Symposium Series, Volume 455 (Marder, et al. eds., 1991)) has demonstrated that organic crystals can have very large nonlinear susceptibilities relative to inorganic crystals, but their use is impeded by their low optical transparencies, poor mechanical properties, low laser damage thresholds, and an inability to produce and process large crystals. Purely inorganic NLO materials typically have excellent mechanical and thermal properties but possess relatively modest optical nonlinearities due to the lack of extended π-electron delocalization. In semiorganics, polarizable organic molecules are stoichiometrically bound within an inorganic host, e.g., an organic ion/inorganic counterion salt, such as L-arginine phosphate, or an organic ligand/metal ion complex, such as zinc tris(thiourea) sulfate (ZTS). Imparting ionic character to large NLO response organic molecules via complexation and/or salt formation works to improve the mechanical and optical properties of crystals of these materials and also provides a high degree of design flexibility for NLO effects utilizing simple synthesis and screening techniques.

The boromalate salts have been identified as potentially useful NLO materials for large-aperture, high average power frequency conversion applications. The salts were crystallized from aqueous solutions containing 2:1:1 molar ratios of L-malic acid to boric acid to the appropriate alkali cation (the latter incorporated as the hydroxide or carbonate). A schematic representation of the boromalate anion is shown in FIG. 1; the trivalent B atom is tetrahedrally coordinated by two malate anions; C* is the chiral carbon atom of the malate anion. Based upon the crystal structure of the potassium salt KBM, the hydroxyl group and adjacent carboxylate hydrogen of each L-malic acid are deprotonated, and two of these dianions tetrahedrally coordinate to the boron(3+) atom, leaving a net minus one charge on the boromalate complex anion. Crystals of salts of this acentric anion are assured of being noncentrosymmetric due to the chirality of the malic acid units. The principal nonlinearities of the boromalates are assumed to arise from delocalized pi-electrons associated with the carboxylate functionalities. It has been observed experimentally that these salts are biaxial and therefore there is the possibility of significant on- and off-axis nonlinear coupling.

Figure 2:
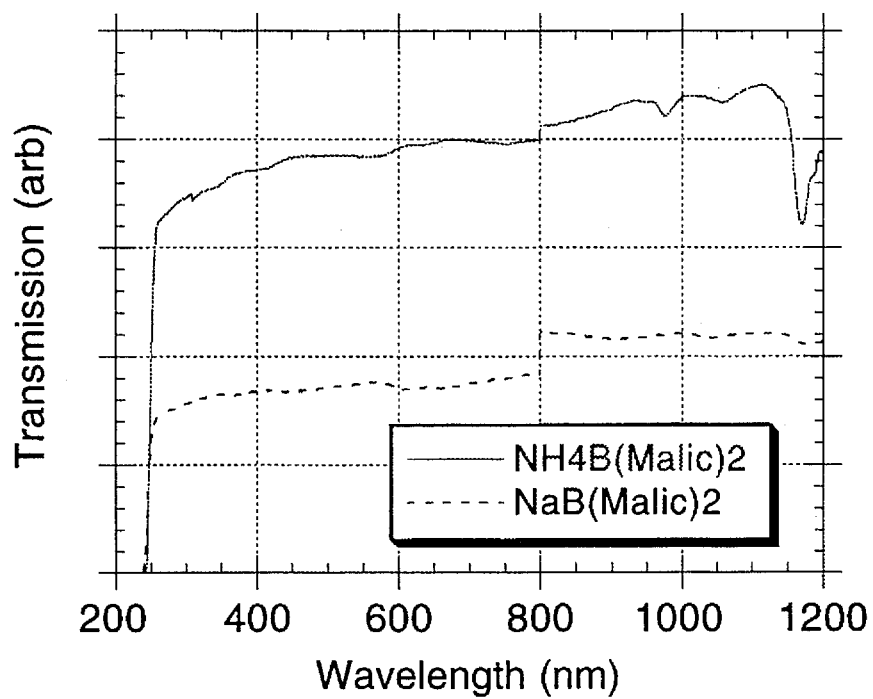
FIG. 2 depicts transmission spectra for ammonia boromalate and sodium boromalate.
Figure 3:
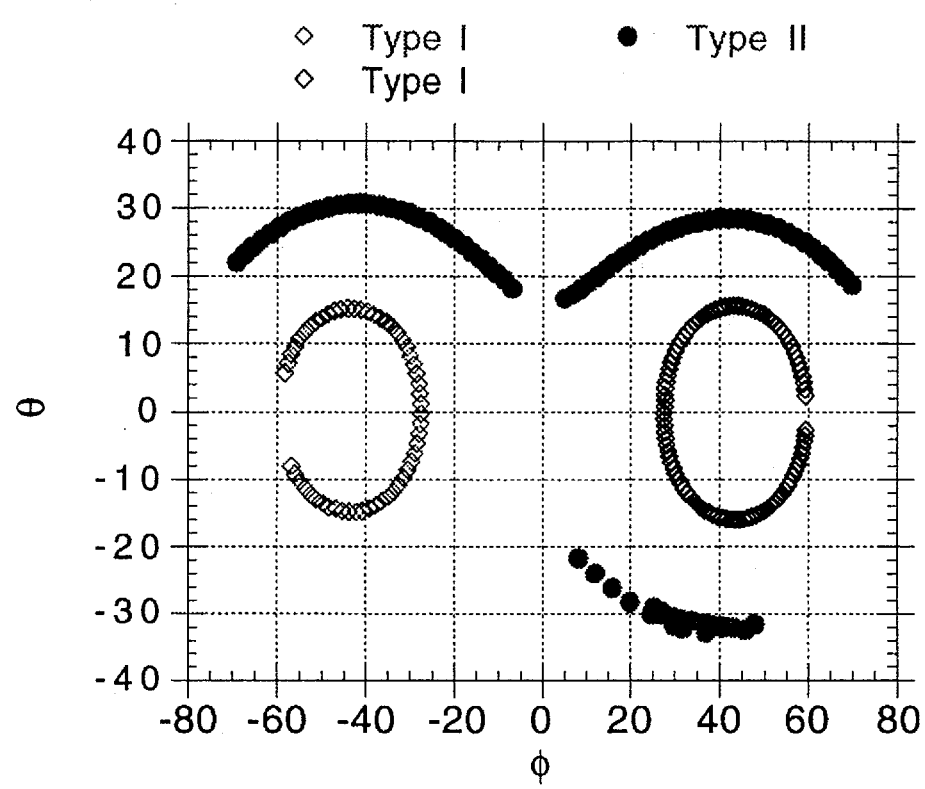
FIG. 3 is a plot depicting the measured phase matching loci for KBM.

The single crystal boromalate salts of this invention are optically transparent between 250 nm and 1300 nm, as shown in FIG. 2, which indicates the transmission spectra for ammonia boromalate and sodium boromalate on unpolished samples of 1.7 mm and 4.1 mm, respectively. The anomaly at 800 nm is due to a grating change in the spectrometer. The measured Type I and Type II 1064 nm second harmonic generation phase matching loci and the corresponding variations of the effective nonlinearities for KBM are shown in FIG. 3 (the bottom left quadrant of the Type II data were not obtainable on this particular sample due to an imperfection in the crystal). In FIG. 3, $\theta=0°$, $\phi=0°$ corresponds to propagation along the dielectric axis having the smallest refractive index and $\theta=\pm90°$, $\phi=0°$ corresponds to propagation along the dielectric axis having the highest refractive index. These data were measured on ~1 mm diameter spheres of KBM using a computer automated version of the direct phase matching (DPM) technique described in Velsko, Optical Engineering, Volume 28, Pages 76–84 (1989). Preliminary analysis of the DPM data indicated that KBM has an effective nonlinearity larger than that of KDP (potassium dihydrogen phosphate) and that it appears to be less angularly sensitive at locations of maximum coupling. The DPM measurement was also performed for ammonium boromalate (NHBM) and indicated a similar nonlinearity and birefringence. The general shape of the phase matching loci indicate that KBM and NHBM probably have sufficient birefringence to phase match for a number of parametric processes between 300 and 1300 nm, including second harmonic generation of 1064 nm light and sum frequency mixing of 1064 nm and 532 nm to produce 355 nm light.

These results suggest that boromalate-based semiorganic salts show great promise as a new NLO material for frequency conversion in the near-IR to near-UV. Because the angular sensitivity appears to be small and relatively constant, the so-called power threshold figure of merit (Eimerl, IEEE Journal of Quantum Electronics, Volume QE-23, Pages 575–592 (1987)) is expected to compare favorably with high temperature melt-grown materials, such as BBO. These results serve to further validate the semiorganic approach to developing solution-grown alternatives to these latter materials.

EXAMPLE 1

Guanidinium Boro-di(1-lactate)

0.020 moles of 1-lactic (Fluka>99%) acid and 0.010 moles of boric acid are dissolved in 10 ml. of water. To this solution, 0.005 moles of guanidine carbonate is added. The solution is stirred until all the guanidine carbonate has reacted. Crystals of guanidinium[B(1-lactate)$_2$] form in the solution as it is evaporated at room temperature.

EXAMPLE 2

Ammonium Boro-di(1-tartrate)

0.010 moles of 1-tartaric acid and 0.005 moles of boric acid are dissolved in 10–15 ml. of water. To this solution, 0.0025 moles of ammonium carbonate, $(NH_4)_2CO_3$, is added. The solution is stirred until all of the ammonium carbonate has reacted. Crystals of $NH_4[B(1$-tartrate$)_2]$ form in solution upon evaporation at room temperature.

EXAMPLE 3

Lithium Boro-di(1-malate)

0.020 moles of 1-malic (Aldrich 99%) acid and 0.010 moles of boric acid are dissolved in 10 ml. of water. To this solution, 0.005 moles of lithium carbonate is added. The solution is stirred until all the lithium carbonate has reacted. Crystals of Li[B(1-malate)$_2$ form in the solution as it is evaporated at room temperature.

EXAMPLE 4

Zinc Boro-di(1-malate)

0.0.10 moles of 1-malic acid and 0.005 moles of boric acid (H3BO3) are dissolved in 10–15 ml. of water. To this solution, 0.0025 moles of zinc carbonate ($ZnCO_3$) is added. The solution is stirred until all zinc carbonate has reacted. Crystals of $Zn[B(1$-malate$)_2]_2.xH_2O$ form in the solution as it is evaporated at room temperature.

EXAMPLE 5

Calcium Boro-di(1-malate)

0.010 moles of 1-malic acid and 0.005 moles of boric acid are dissolved in 10–15 ml. of water. To this solution, 0.0025 moles of calcium carbonate ($CaCO_3$) is added. The solution is stirred until all the calcium carbonate has reacted. Crystals of $Ca[B(malate)_2]_2.xH_2O$ form in the solution as it is evaporated at room temperature.

EXAMPLE 6

Potassium Boro-di(dimethyl-1-tartrate)

0.020 moles dimethyl-1-tartrate and 0.010 moles of boric acid are dissolved in 10 ml. of water. To this solution, 0.005 moles of potassium carbonate ($K_2CO_3$) is added. The solution is stirred until all of the potassium carbonate has reacted. Crystals of K[B(dimethyl-1-tartrate)$_2$] form in the solution as it is evaporated at room temperature.

EXAMPLE 7

Sodium Boro-di(diethyl-1-tartrate)

0.020 moles of diethyltartaric acid and 0.010 moles of boric acid are dissolved in 10ml. of water. To this solution, 0.005 moles of sodium carbonate ($Na_2CO_3$) is added. The solution is stirred until all of the sodium carbonate has reacted. Crystals of Na[B(diethyl-1-tartrate)$_2$] form in the solution as it is evaporated at room temperature.

EXAMPLE 8

Potassium Boro-di(ethylene glycolate)

0.020 moles of ethylene glycol and 0.010 moles of boric acid are dissolved in 10 ml. of water. To this solution, 0.005 moles of potassium carbonate ($K_2CO_3$) is added. The solution is stirred until all of the potassium carbonate has reacted. Crystals of K[B(ethyleneglycolate)$_2$] form in the solution as it is evaporated at room temperature.

The preferred embodiments of this invention have been illustrated by the examples described above. Modifications and additional embodiments, however, will undoubtedly be apparent to those skilled in the art. Furthermore, equivalent elements may be substituted for those illustrated and described herein. For example, variations of the two crystals could include the deuterated analogs (the hydrogen atoms, H, substituted with deuterium atoms, D) which could extend the useful wavelength range of the materials further into the infrared. Consequently, the exemplary embodiments should be considered illustrative, rather than inclusive, while the appended claims are more indicative of the full scope of the invention.

The teaching of the following documents, which are referred to herein, is incorporated by reference:

Bierlein, et al., U.S. Pat. No. 3,949,323.

Dong, et al., A New Aromatic Organometallic Nonlinear Optical Crystal: [Bis-4-nitropyridine-N-oxide Cadmium Chloride], Materials Research Bulletin, Volume 29, Page 73 (1994).

Eimerl, IEEE Journal of Quantum Electronics, Volume QE-23, Pages 575–592 (1987).

Marcy, et al., Applied Optics, Volume 31, Pages 5051–5060 (1992).

Materials for Nonlinear Optics-Chemical Perspectives, American Chemical Society Symposium Series, Volume 455 (Marder, et al. eds., 1991).

Meredith, in Nonlinear Optical Properties of Organic and Polymeric Materials, American Chemical Society Symposium Series, Volume 233, Pages 27–56 (Williams ed., 1982).

Velsko, Optical Engineering, Volume 28, Pages 76–84 (1989).

Warren, in Electronic Materials-Our Future, Proceedings of the 4th International SAMPE Electronics Conference, Volume 4, Pages 388–396 (Allred, et al. eds., 1990).

Wenbo et al., A new organometallic nonlinear optical material-triallylthiourea mercury bromide (ATMB) crystal: growth and structure, Journal of Crystal Growth, Volume 133, Page 71 (1993).

We claim:

1. A nonlinear optical material, which is a noncentrosymmetric crystal of an anionic boron complex salt containing a cation and at least one organic ligand coordinated to a boron atom, wherein the anionic boron complex is selected from the group consisting of boro-di(l-malate), boro-di(l-tartrate), boro-di(l-lactate), boro-di(diethyl-l-tartrate), boro-di(dimethyl-l-tartrate), boro-di(d-malate), boro-di(d-tartrate), boro-di(d-lactate), boro-di(diethyl-d-tartrate), boro-di(dimethyl-d-tartrate) and boro-di(ethylene glycolate), the cation is selected from the group consisting of lithium, sodium, potassium, the ammonium ion, the guanidinium ion, calcium, and zinc.

* * * * *